United States Patent [19]

McGregor et al.

[11] Patent Number: 4,716,757
[45] Date of Patent: Jan. 5, 1988

[54] GUIDE WIRE TIP SHAPING TOOL AND METHOD

[75] Inventors: Jean E. McGregor, Sunnyvale; Wilfred J. Samson, Saratoga; Craig E. Mar, Fremont, all of Calif.

[73] Assignee: Advanced Cardiovascular Systems, Inc., Mountain View, Calif.

[21] Appl. No.: 900,046

[22] Filed: Aug. 25, 1986

[51] Int. Cl.⁴ .............................................. B21F 1/00
[52] U.S. Cl. ...................................... 72/387; 72/383; 72/458; 140/106
[58] Field of Search ............... 72/387, 383, 457, 458; 140/106; 29/505, 423

[56] References Cited

U.S. PATENT DOCUMENTS

| | | | |
|---|---|---|---|
| 951,717 | 3/1910 | Andres | 72/381 |
| 3,248,921 | 5/1966 | Trout | 72/458 |
| 3,824,834 | 7/1974 | Durham | 72/387 |
| 3,888,101 | 6/1975 | Crees | 72/458 |
| 4,315,422 | 2/1982 | McBride | 72/458 |

Primary Examiner—Robert L. Spruill
Assistant Examiner—David B. Jones
Attorney, Agent, or Firm—Fulwider, Patton, Rieber, Lee & Utecht

[57] ABSTRACT

Tool and method for bending of shaping the tips of angioplasty guide wires. The tool has two relatively rigid body sections joined together by a relatively flexible hinge, with a flexible tube extending across the hinge for holding the tip of the wire to be bent. The body sections are folded together about the hinge to bend the wire, and the flexible tube tends to form a kink in the wire which helps the wire to retain the shape to which it is bent. Stops limit the movement of the body sections and prevent overbending of the wire.

13 Claims, 5 Drawing Figures

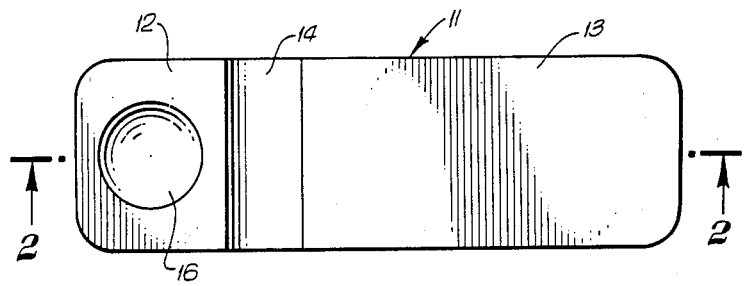
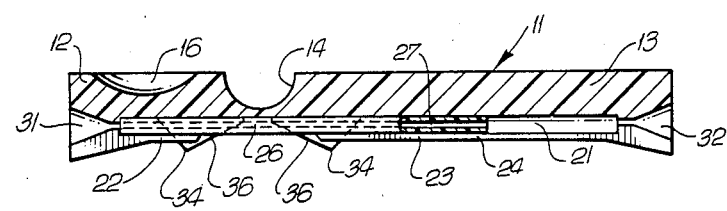
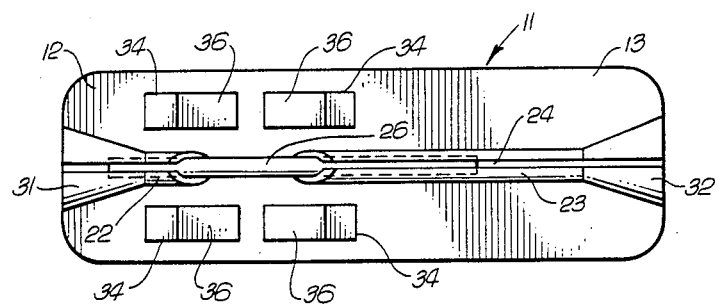
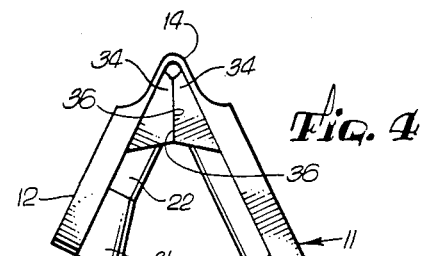
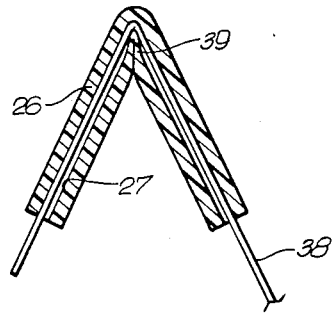

ns of tue angioplasty guide wires.
GUIDE WIRE TIP SHAPING TOOL AND METHOD

This invention pertains generally to medical appliances, and more particularly to a tool and method for bending or shaping the tips of guide wires used in angioplasty.

The insertion of guide wires used in angioplasty can sometimes be facilitated by bending or shaping the tips of the wires prior to insertion. The shaping or bending of the tip can make it easier for the doctor to steer the wire through the vascular system to the desired vessel. The tips of many guide wires are relatively fine and difficult to grip for bending or shaping, particularly when they are coated with a lubricious material to make them pass more easily through the vascular system.

It is in general an object of the invention to provide a new and improved tool and method for bending or shaping the tips of angioplasty guide wires.

Another object of the invention is to provide a tool of the above character which is economical to manufacture and easy to use.

These and other objects are achieved in accordance with the invention by providing a tip shaping tool having first and second body sections connected hingedly together and movable to different angular positions relative to each other. Means is carried by the two body sections for holding the tip of the guide wire so that the tip can be bent by moving the body sections from one angular position to another. In the disclosed embodiment, the means for holding the tip comprises a flexible tube which extends across the hinged connection with an axially extending opening which receives the tip. A funnel shaped guide facilitates insertion of the tip into the opening, and stop members carried by the body sections limit the angular movement between the two body sections and prevent overbending of the wire.

FIG. 1 is a top plan view of one embodiment of a guide wire tip shaping tool according to the invention.

FIG. 2 is a cross-sectional view taken along line 2—2 in FIG. 1.

FIG. 3 is a bottom plan view of the embodiment of FIG. 1.

FIG. 4 is a operational side elevational view illustrating the use of the embodiment of FIG. 1 for bending the tip of a guide wire.

FIG. 5 is an enlarged, fragmentary sectional view further illustrating the operation of the embodiment of FIG. 1.

As illustrated in the drawings, the tip shaping tool has a generally planar body 11 having a pair of generally rectangular body sections 12, 13 connected together by a hinge 14. The body is fabricated of a relatively rigid plastic material such as polyethylene, and the hinge is formed as an area of reduced thickness between the two body sections. The body sections are of different lengths, with section 13 being about twice as long as section 12. A recessed area 16 is formed in the upper surface of section 12 to facilitate gripping of this section.

A channel 21 is formed on the underside of body 11 for holding the tip of the guide wire to be bent. The channel is formed in a pair of axially aligned ribs 22, 23 on the undersides of the respective body sections. The channel has a generally circular cross-section, and it opens through a slot 24 in the ribs.

A tube 26 of flexible material such as rubber is mounted in channel 21 and extends across hinge 14. The tube has an axially extending opening 27 in which the tip of the guide wire is received. The opening in the tube is slightly larger than the tip of the guide wire, and as described more fully hereinafter, the relatively flexible tube serves to kink the wire as it is bent so that it will retain its shape.

Funnel shaped guides 31, 32 are formed at the outer ends of ribs 22, 23. These guides are axially aligned with the opening in flexible tube 26, and they facilitate insertion of the guide wire into the opening.

Stops 34 are mounted on the underside of the body to limit the movement of body sections 12, 13 when the body is flexed about hinge 14. The stops are arranged in pairs on opposite sides of channel 21, and they have inclined faces 36 which abut against each other to limit the movement of the body sections. In one presently preferred embodiment, the faces are inclined at an angle on the order of 25° relative to the lower surface of the body, and the body sections can be moved within about 50° of each other.

Body 11, ribs 22, 23, guides 31, 32 and stops 34 are fabricated as a unitary structure of a relatively rigid plastic material such as polyethylene. This structure can be made by a molding process, and the tool is inexpensive enough to be disposable. It can, for example, be packaged with a guide wire and thrown away after a single use. The flexible tube 26 is inserted into channel 21 through confronting openings at the inner ends of the ribs.

Operation and use of the tip shaping tool, and therein the method of the invention, are best understood with reference to FIGS. 4 and 5. The tip 38 of a guide wire is inserted into the opening in flexible tube 27 through one of the funnel shaped guides 31, 32 and positioned with the portion of the wire to be bent opposite hinge 14. Thereafter, the two body sections are gripped by the hands of the doctor and moved toward each other about hinge 14 until the desired degree of bending is achieved. As the hinge flexes, the wall portion of flexible tube 26 on the inside of the bend collapses, forming a somewhat resilient mandrel 39 which bears against the side of the wire and tends to kink the wire and help it retain the shape to which it is bent.

The angle to which the wire can be bent is limited by stops 34. If a greater degree of bending is desired, the wire can be repositioned and bent again until the desired shape is achieved.

The tip of the guide wire can be inserted into the tool from either end of the body. The short end (section 12) is particularly useful for the guide wires which cannot be inserted far enough into the long end (section 13) to bend the desired portion of the wire. This can happen, for example, with certain dilatation catheters having the guide wire as an integral part thereof, with a balloon which prevents the tip from being inserted far enough through the larger section.

The invention has a number of important features and advantages. The tool is economical to manufacture and easy to use, and it enables doctors to shape wires which would otherwise be difficult to bend.

It is apparent from the foregoing that a new and improved tool and method for bending angioplasty guide wires have been provided. While only certain presently preferred embodiments have been described in detail, as will be apparent to those familiar with the art, certain changes and modifications can be made without departing from the scope of the invention as defined by the following claims.

We claim:

1. In a tool for bending the tip of an angioplasty guide wire; first and second body sections, hinge means connecting the body sections together and permitting the body sections to be moved to different angular positions relative to each other, and a flexible tube extending between the two body sections and having an axial opening for holding the tip of the guide wire so that the tip can be bent by moving the body sections from one angular position to another.

2. The tool of claim 1 including a funnel shaped guide carried by one of the body sections in axial alignment with the opening in the tube to facilitate insertion of the guide wire into the tube.

3. The tool of claim 1 including stop means carried by one of the body sections to limit angular movement between the body sections.

4. The tool of claim 1 wherein the two body sections and the hinge means are fabricated as a unitary structure of relatively rigid material, the hinge means comprising an area of reduced thickness between the body sections.

5. The tool of claim 1 wherein the flexible tube extends continuously and without interruption across the hinge means.

6. The tool of claim 4 wherein the flexible tube so fabricated of a relatively flexible material and is mounted on the unitary structure.

7. In a tool for bending the tip of an angioplasty guide wire: a generally planar body of plastic material having a pair of rigid body sections and an area of reduced thickness forming a relatively flexible hinge between the body sections, a flexible tube mounted on one side of the generally planar body and extending across the area of reduced thickness with an axially extending opening for receiving the tip of the guide wire and holding the tip for bending as the body is flexed about the hinge.

8. The tool of claim 6 including a funnel shaped guide carried by one of the body sections in axial alignment with the opening in the tube to facilitate insertion of the guide wire into the tube.

9. The tool of claim 6 wherein the end portions of the flexible tube are mounted in channels on the one side of the generally planar body.

10. The tool of claim 7 including stop means carried by one of the body sections for limiting movement of the body sections upon flexing of the body.

11. In a method of bending the tip of an angioplasty guide wire with a tool having a pair of body sections joined together by a hinge and a flexible tube having an axial opening extending between the body sections, the steps of: inserting the tip of the guide wire into the axial opening of the flexible tube so that the guide wire extends across the hinge, and folding the body sections together about the hinge to bend the flexible tube and the tip of the wire inserted therein.

12. The tool of claim 7 wherein the flexible tube extends continuously and without interruption across the area of reduced thickness.

13. The tool of claim 7 wherein the flexible tube is formed separately from the body.

* * * * *